United States Patent [19]
DiFrancesco

[11] Patent Number: 5,868,786
[45] Date of Patent: Feb. 9, 1999

[54] INTEGRAL LOG LINKAGE FOR MICRO-INSTRUMENT

[75] Inventor: Francis J. DiFrancesco, Foxboro, Mass.

[73] Assignee: TNCO, Inc., Whitman, Mass.

[21] Appl. No.: 843,563

[22] Filed: Apr. 18, 1997

[51] Int. Cl.[6] .................................................. A61B 17/28
[52] U.S. Cl. ..................... 606/208; 606/205; 606/170; 606/174
[58] Field of Search .................................. 606/170, 174, 606/205, 206, 207, 208; 30/266; 81/416

[56] References Cited

U.S. PATENT DOCUMENTS

| | | | |
|---|---|---|---|
| 2,214,985 | 9/1940 | Bachmann | 81/303 |
| 2,632,661 | 3/1953 | Cristofv | 403/119 |
| 5,152,780 | 10/1992 | Honkanen et al. | 606/205 |
| 5,219,357 | 6/1993 | Honkanen et al. | 606/205 |

Primary Examiner—Michael Buiz
Assistant Examiner—David O. Reip
Attorney, Agent, or Firm—Stephen Y. Chow, Esq.; Jerry Cohen, Esq.

[57] ABSTRACT

A articulating tip structure with a pivot lug and a rotatable jaw with a pivot seat which wraps around the lug in normal operation and provides a gap for disengagement of the lug to allow disassembly and assembly.

54 Claims, 7 Drawing Sheets

INTEGRAL LOG LINKAGE FOR MICRO-INSTRUMENT

BACKGROUND OF THE INVENTION

The field of the invention is that of micro-instrumentation, that is, articulating, hand-held, instruments used in micro-surgery, electronic micro-assembly and like applications, for grasping, cutting, punching out, probing and the like. The instruments can comprise scissors-handle actuators, so-called cigar handle linear or rotary activators, or other actuators, with push or pull force application design modes.

The invention is particularly advantageous for endoscopic, or minimally invasive, surgery, but is also advantageous in other applications for micro-instrumentation.

Prior art endoscopic surgical instruments are shown in U.S. Pat. No. 5,152,780 to Honkanen et al. and U.S. Pat. No. 5,219,357 to Honkanen et al., which disclose, respectively, the use of one or two jaws rotatably mounted on one or two pivots that are integrally formed with a wall that is part of the frame of the instrument, while a linkage mechanism movable relative to that wall effects rotation of the jaw or jaws. The integral nature of the pivot or pivots provided the advantages of resulting in fewer parts to assemble and possibly accidentally disassemble inside a patient and of providing strength to the working portion of the instruments, avoiding breakage inside a patient.

A disadvantage of the integral pivot mechanisms disclosed in the prior art arises from the fact that the jaws disclosed therein are provided with a straight slot ending in a semicircular bearing surface which engages or seats an integral pivot of cylindrical or hour-glass shape. The straight slot, along which the pivot slides in assembly, also provides an unwanted degree of freedom in operation. Thus, in the disclosed mechanism, when the jaw is pulled proximally to the operator to open the jaw, the jaw may slip linearly along the slot relative to the pivot until the jaw hits a bulkhead, which, for example is explained at U.S. Pat. No. 5,152,780, col. 3, lines 25–28, as a "ramp surface" of the outer tip assembly including the pivot wall. Close tolerance with the ramp surface is difficult and therefore expensive to achieve, while a wider gap results in unwanted "play", uneven wear, and even the possibility of lodging of unwanted debris.

SUMMARY OF THE INVENTION

It is a particular objective of the present invention to provide an endoscopic instrument that is rotatable at the jaws with little play between the parts to assure tactile sense by the user, for example, a surgeon, to minimize wear, and to minimize areas for lodging of debris.

It is a further objective to provide an endoscopic instrument that is as strong as possible in its working components.

The present invention comprises a lug of generally circular cross section with at least one flat surface and a jaw rotatable on that pivot with an access to the generally circular pivot seat through an opening smaller than the diameter of the circular cross section of the lug and larger than the thickness of the lug measured at the flat surface. Once assembled by inserting the lug, rotated to present its narrower aspect, through the opening, then rotating the assembly to its operating orientation, the circular overwrap of the pivot seat holds the lug pivot securely against lateral play.

The present invention meets the objectives mentioned and has a number of other advantages that will be apparent from the detailed description of the preferred embodiment, including relative ease of manufacture of the components.

DETAILED DESCRIPTION

Figure 1:
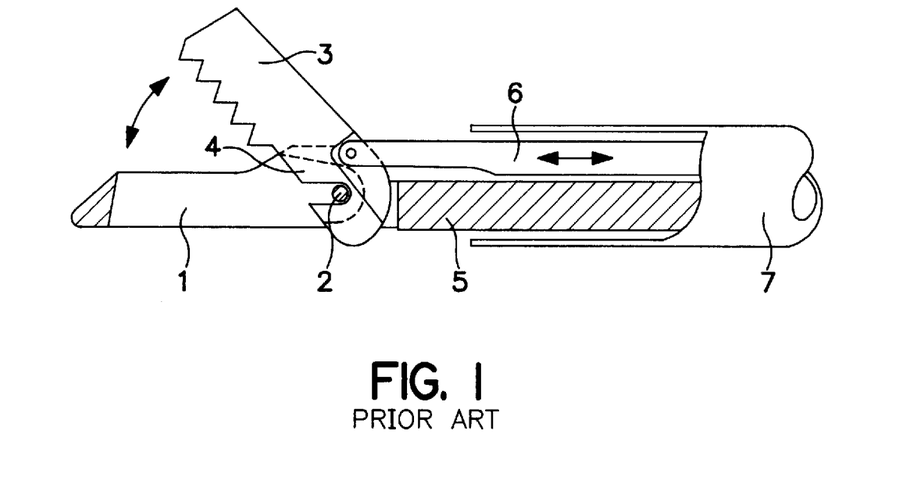
FIG. 1 is a side view of a prior art instrument.

FIG. 1 shows the prior art of U.S. Pat. No. 5,152,780. A tip support structure 1 is connected relatively rigidly with bulkhead 5 and tubular extension 7. Actuating or driving link 6, which reciprocates according to control by the operator typically by a movable handle (not shown), moves jaw 3 around pivot 2 to open and closed positions. In this embodiment, link 6 pushes jaw 3 to close. In other embodiments, link 6 may be further linked using a scissors-type linkage. In the shown embodiment, link 6 is pulled to the right to open jaw 3. This may cause lateral slippage of jaw 3 along slot 4, limited only by bulkhead 5.

Figure 2:
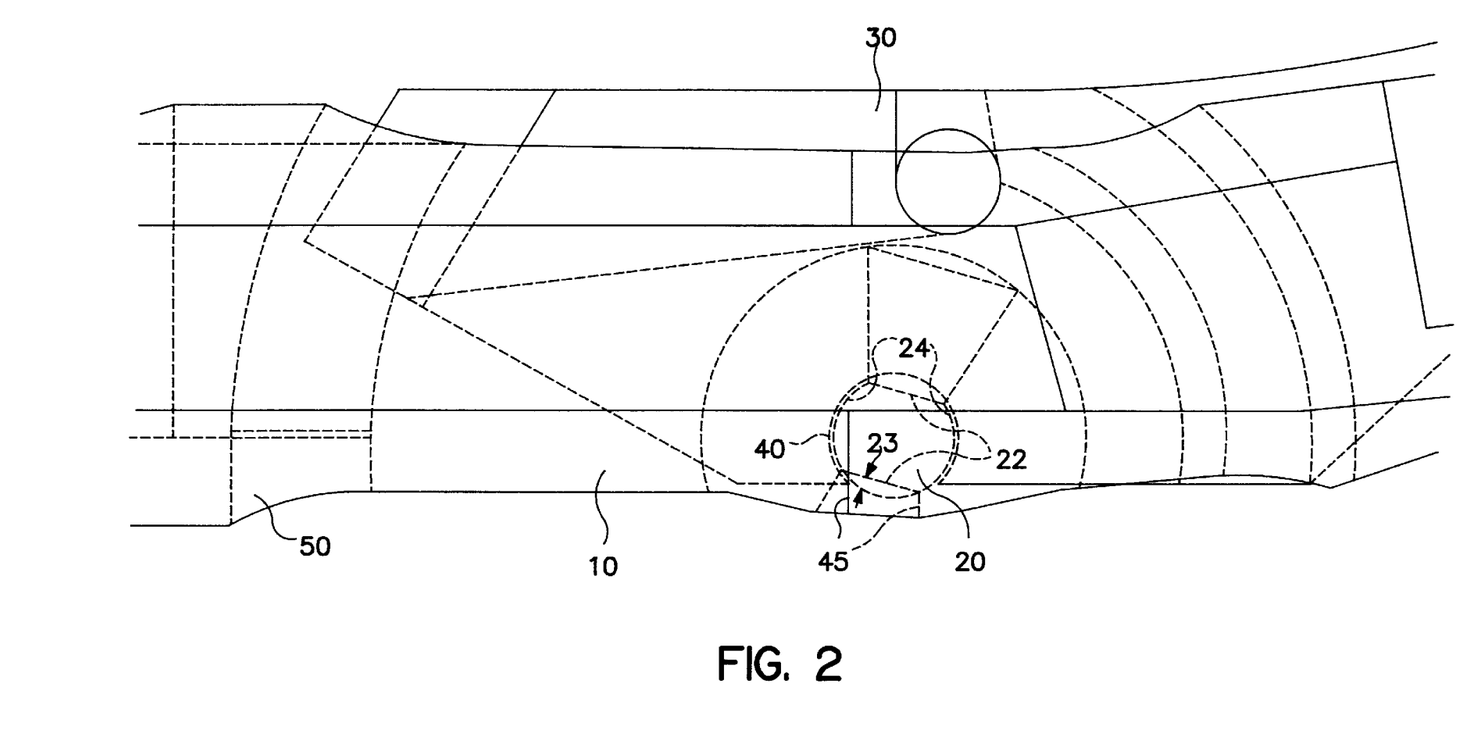
FIG. 2 is a detailed side view of the invention with jaw close.
Figure 2A:
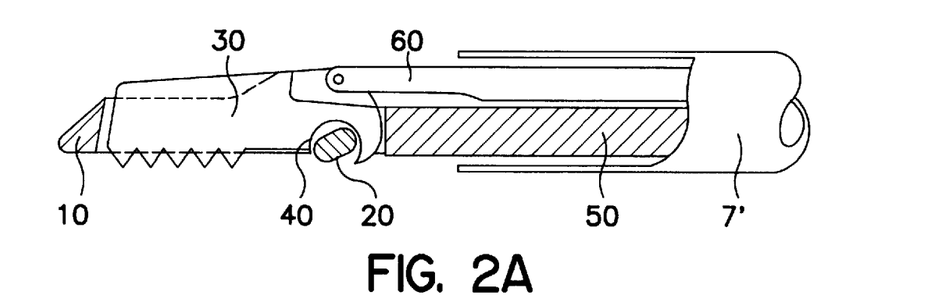
FIG. 2A is a side view of an instrument including the present invention with jaw opened.

FIG. 2A shows a side view of the invention in a preferred embodiment, with jaw closed. A tip support structure 10 is connected relatively rigidly with bulkhead 50 and tubular extension 70. Actuating or driving link 60 has been extended to move jaw 30 around pivot 20 to a closed position. FIG. 2 shows the detail of the pivot lug 20 and pivot seat 40. Pivot seat 40 defines a portion of a circle with a gap 45 corresponding to an arc of about 40°. Pivot lug has a cross section in an area defined by a circle of slightly smaller diameter with two parallel cuts 22 forming chords of the circle and tilted 23 slightly upwards, for example, by 15°, at the proximal end relative the jaw action at the distal end. The arcs 24 at each end of the cuts 22 are equal to or less than the arc of gap 45.

Figure 3:
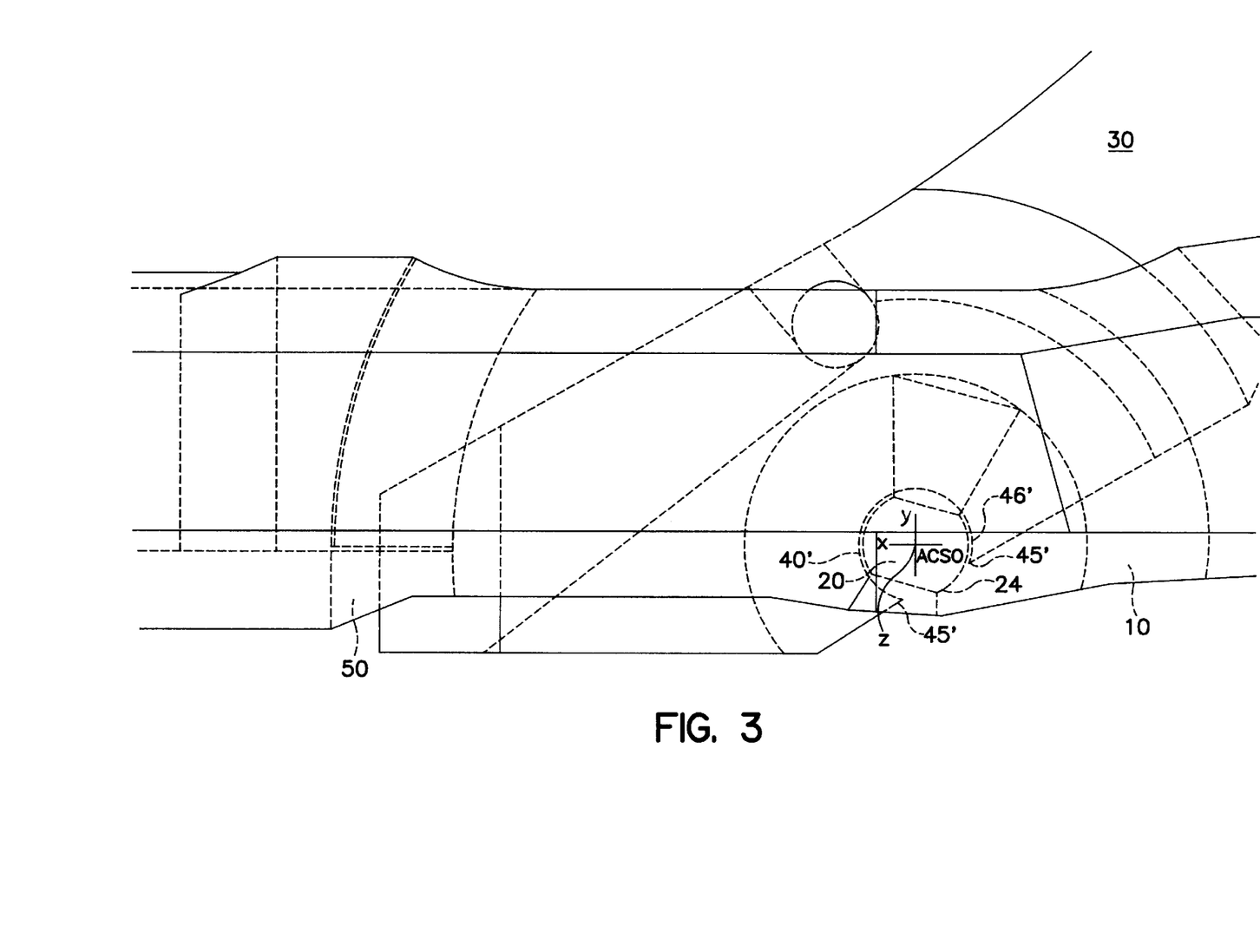
FIG. 3 is a detailed side view of the invention with jaw open.
Figure 3A:
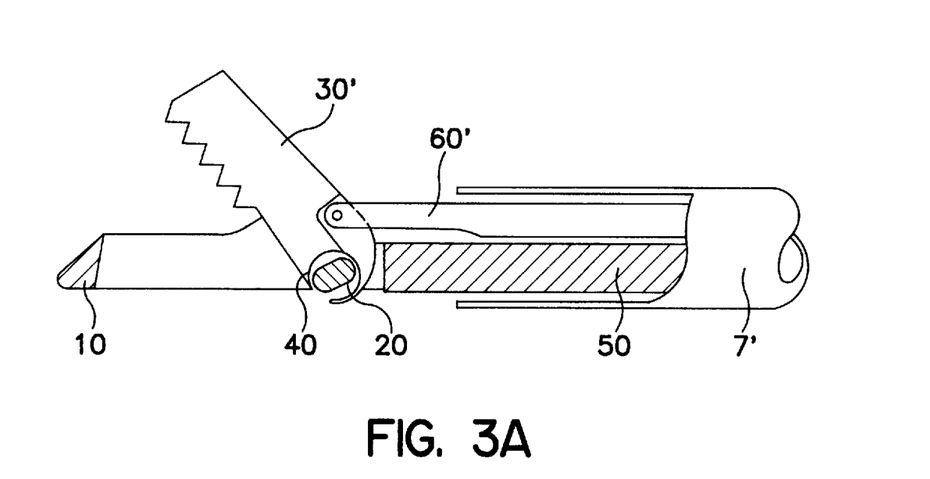
FIG. 3A is a side view of an instrument including the present invention with jaw opened.

FIG. 3A shows a side view of the invention in a preferred embodiment, with jaw open. Actuating or driving link 60' has been retracted to move jaw 30' around pivot 20 to an open position. Bulkhead 50 does not necessarily engage jaw 30'. FIG. 3 shows the detail of the pivot lug 20 and pivot seat 40'. Engagement of arc 24 with overwrap 46' provides limitation to lateral motion of jaw 30' relative to tip structure 10.

Figure 4:
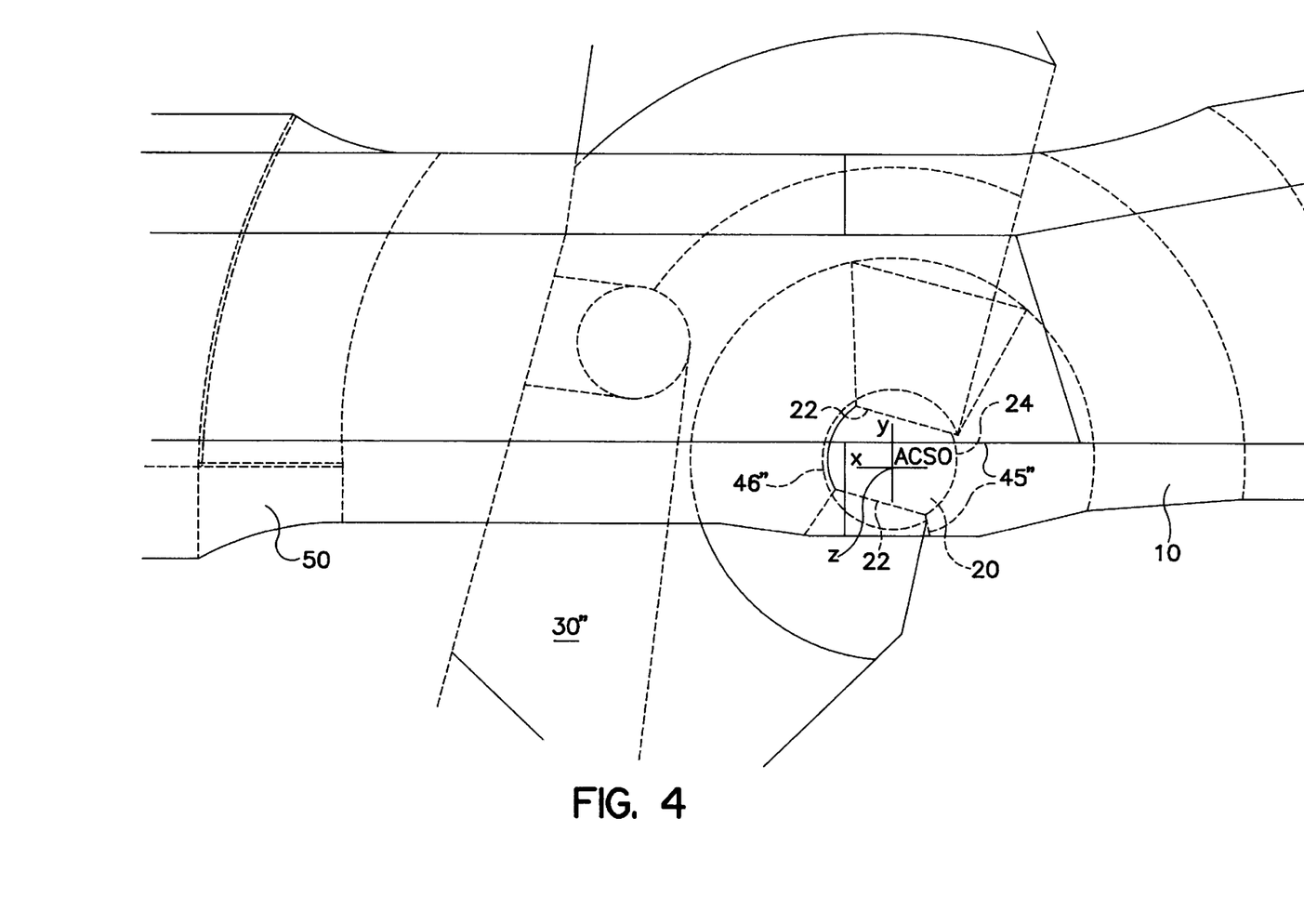
FIG. 4 is a detailed side view of the invention with the jaw rotated to a position for removal from the tip support structure.
Figure 5:
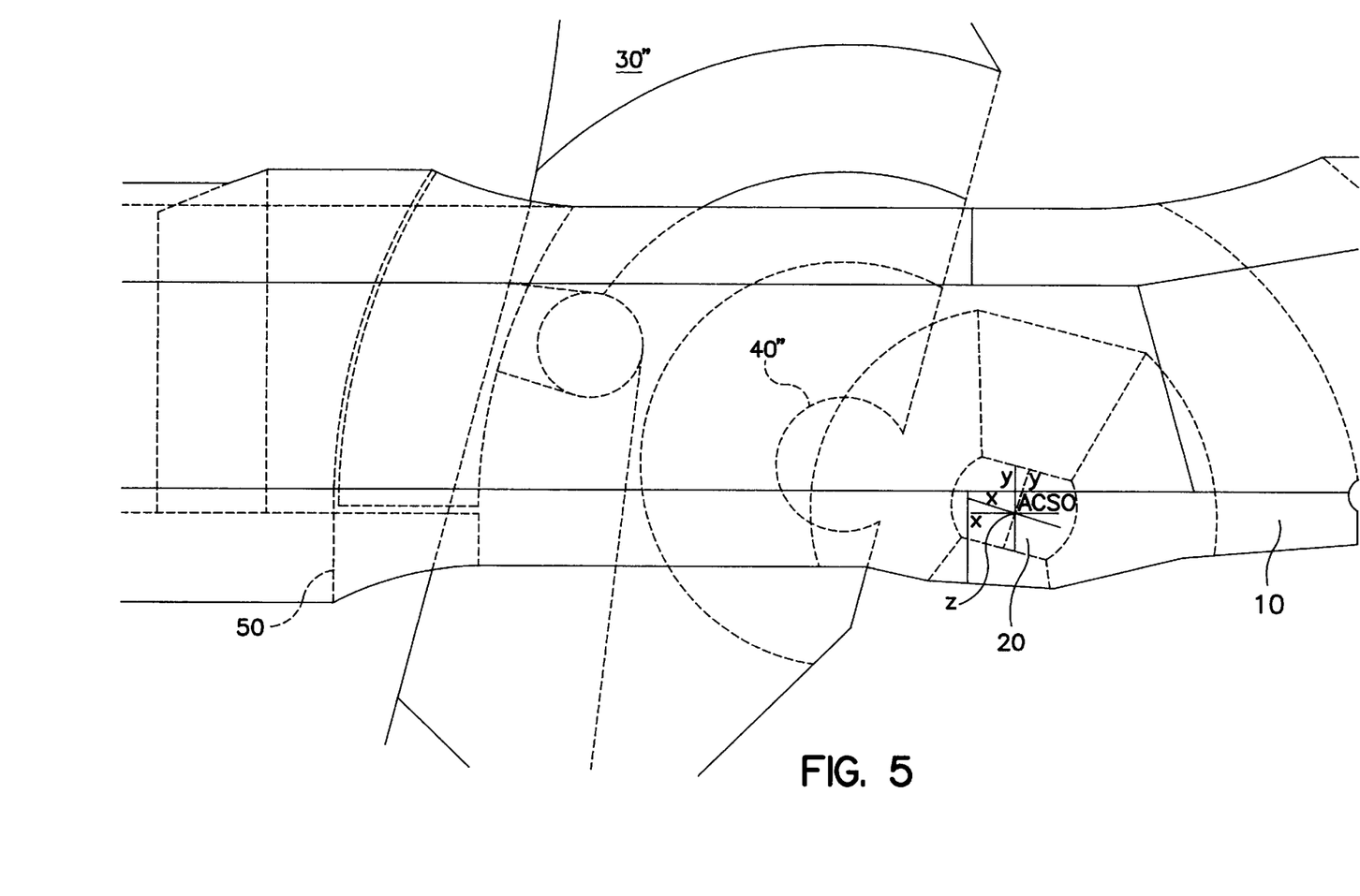
FIG. 5 is a detailed side view of the invention with the jaw removed from engagement with the pivot.

FIG. 4 shows a detail of the pivot lug 20 and pivot seat 40" when jaw 20" has been rotated further than the open position, for example, by approximately 40°, to a position in which it may be disengaged from pivot lug 20 and the tip support structure 10. It can be seen that arc 24 is the same or slightly smaller than the arc of gap 45", and with parallel cuts 22 relatively straight (flat in three dimensions), lug 20 may be moved out through gap 45". FIG. 5 shows a detail of the disengaged configuration, in which lug 20 is entirely clear of lug seat 40"'.

Figure 6:
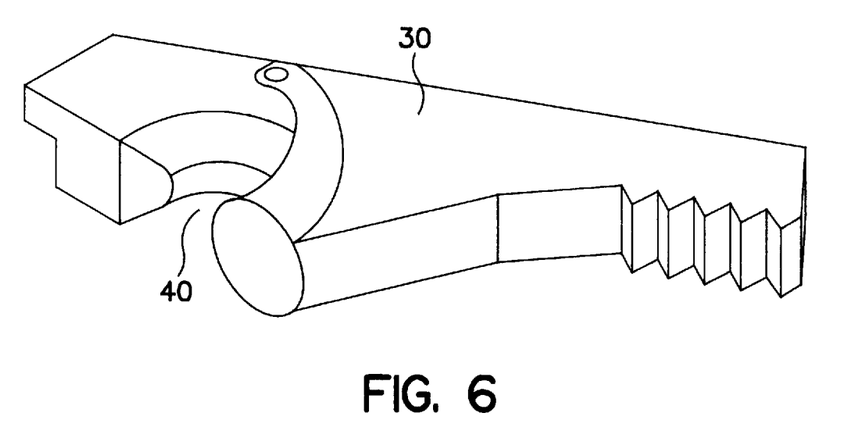
FIG. 6 is an isometric view of a jaw used in the present invention.
Figure 7:
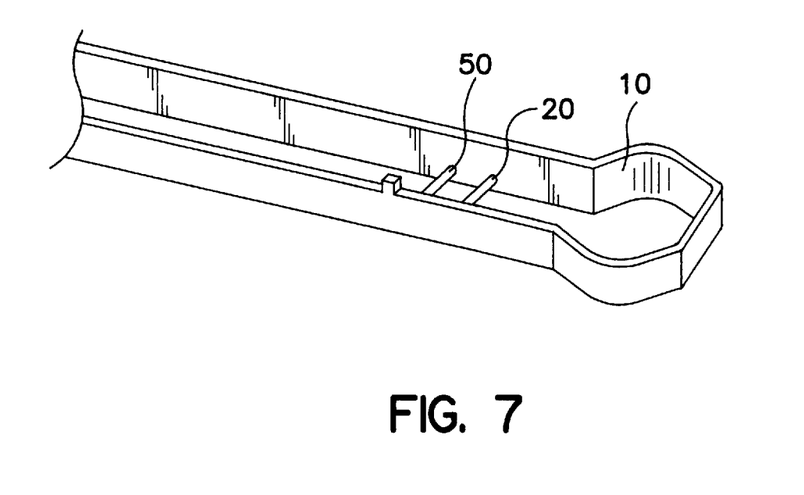
FIG. 7 is an isometric view of a tip structure used in the present invention.

FIGS. 6 and 7 show, respectively, a preferred embodiment of the invention in which lug 20 is disposed between walls of the tip support structure 10 and has an hourglass shape (thicker near the walls) prior to the parallel cuts. In a metallic (as opposed to molder plastic) configuration, lug seat 40 can be formed by turning on a lathe, then cutting to form gap 45. Lug 20 may be milled full round by a ball mill, then the same ball mill may be used to make cuts 22. This shows the additional advantage of using different specialized machines for fabricating the jaws and the lugs.

As can be seen, the invention may find application with one wall support or two, with a cylindrical lug or other shaped lung, with one jaw or two.

Figure 8:
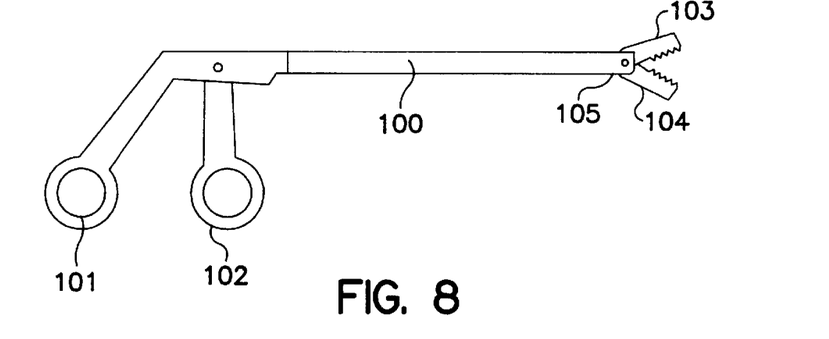
FIG. 8 shows an endoscopic instrument employing a two-jaw version of the invention.

Thus, FIG. 8 shows an endoscopic instrument employing a two-jaw version of the invention, where supporting extension shaft 100 contains an unshown drive shaft which is linked to jaws 103 and 104 of general construction like that shown in FIG. 6. Invisible lug 105 which may extend between parallel walls, as lug 20 in FIG. 7, may support both jaws. Handle 101 with a finger loop is stationary and handle 102 with a finger loop is moveable to push the drive shaft forward as shown in FIG. 2A and FIG. 3A.

Figure 9:
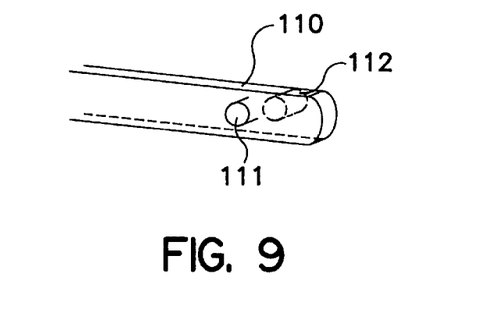
FIG. 9 shows a detail of a pair of cylindrical integral lugs on either side of a mounting wall that may be used in a two-jaw application of the invention.
Figure 10:
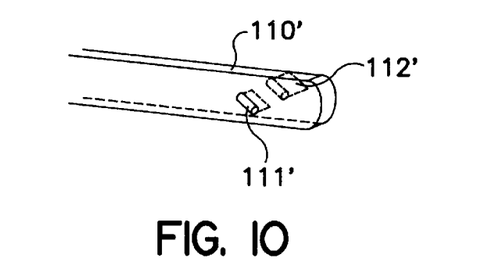
FIG. 10 shows a detail of a pair of cylindrical sectional integral lugs on either side of a mounting wall that may be used in a two-jaw application of the invention.
Figure 11:
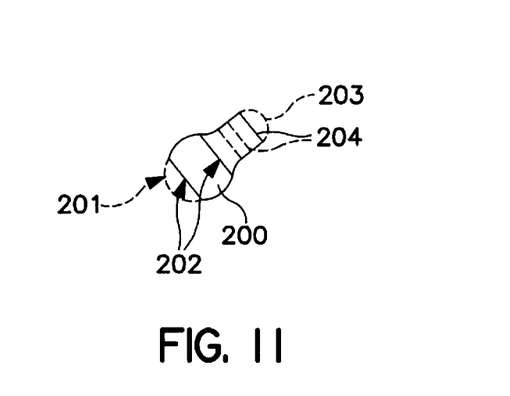
FIG. 11 shows details of a half-hourglass lug section that may be used in the invention.

FIG. 9 shows a detail of a pair of cylindrical integral lugs 111 and 112 on either side of a mounting wall 110 that may be used in a two-jaw application of the invention as shown in FIG. 8 instead of lug 105. FIG. 10 shows a detail of a pair of integral lugs 111' and 112' formed from cylinders milled for form opposite flat faces and positioned on either side of a mounting wall that may be used in a two-jaw application of the invention. FIG. 11 shows details of a lug section 200 formed in a half-hourglass shape with larger-diameter circle 201 forming the shape of the flared end and smaller-diameter circle 203 forming the shape of the smaller end, with flat cuts 202 and 204 forming edges allowing access of a jaw like that shown in FIG. 6. In each embodiment, the lug or lugs may be fabricated separately, although it is preferably integral to the tip support structure.

What is claimed is:

1. A miniature articulating tip assembly comprising:
   (a) a tip support structure;
   (b) a lug connected substantially orthogonally to a portion of said support structure, said lug having a first cross section consisting of an area defined by a portion of a first circle with at least one cut roughly forming a chord of said circle and said area spanning at at least one chord the diameter of said circle; and
   (c) a jaw rotatable relative to said tip support structure, said jaw having a pivot seat for seating said lug and rotatably engaged at said pivot seat with said lug, said pivot seat defining at a cross section corresponding with said first cross section, a portion of a second circle of diameter greater than the diameter of said first circle with a gap of 180° or less of arc through which said lug may be seated and unseated when rotated relative to said jaw; wherein said tip support structure provides two substantially parallel walls connected by said lug and between which said jaw rotates.

2. The apparatus of claim 1 wherein said lug is fabricated as a single piece with said tip structure support.

3. The apparatus of claim 2 wherein said lug is of hourglass shape with a portion cut parallel to its axis.

4. The apparatus of claim 3 wherein said lug is fabricated as a single piece with said tip structure support.

5. The apparatus of claim 2 wherein said lug is a cylinder with two equal portions cut away parallel to the lug axis a parallel to each other on opposite sides of the lug axis.

6. The apparatus of claim 5 wherein said parallel cuts define between each other equal arcs on said first circle of approximately 40° each and said gap on said second circle is approximately 40°.

7. The apparatus of claim 6 wherein said jaw is rotated by a force applied parallel to a longitudinal axis of said tip support structure and said parallel cuts are made at an angle of approximately 15° rotation from said longitudinal axis.

8. The apparatus of claim 2 wherein said lug of hourglass shape with two equal portions cut away parallel to the lug axis and parallel to each other on opposite sides of the lug axis.

9. The apparatus of claim 8 wherein said parallel cuts define between each other equal arcs on said first circle of approximately 40° each and said gap on said second circle is approximately 40°.

10. The apparatus of claim 9 wherein said jaw is rotated by a force applied parallel to a longitudinal axis of said tip support structure and said parallel cuts are made at an angle of approximately 15° rotation from said longitudinal axis.

11. The apparatus of claim 1 wherein said lug is cylindrical with a portion cut parallel to its axis.

12. The apparatus of claim 11 wherein said lug is fabricated as a single piece with said tip structure support.

13. A miniature articulating tip assembly comprising:
   (a) a tip support structure defining parallel walls on either side of a longitudinal axis including a lug connecting said walls, said lug being of a solid of revolution with two equal portions cut away parallel to the lug axis and parallel to each other on opposite sides of the lug axis; and
   (b) a jaw rotatable relative to said tip support structure by a force applied parallel to said longitudinal axis of said tip support structure, said jaw having a pivot seat for closely seating and rotatably engaging said lug with a negative form of said solid of revolution with a gap provided slightly larger than the distance between said parallel cuts.

14. The apparatus of claim 13 wherein said solid of revolution is a cylinder.

15. The apparatus of claim 14 wherein said solid of revolution is or hourglass shape.

16. The apparatus of claim 13 wherein said lug is fabricated as a single piece with said walls.

17. The apparatus of claim 13 wherein said parallel cuts define between each other equal arcs on said solid of revolution of approximately 40° each and said gap on said negative solid of revolution is approximately 40°.

18. The apparatus of claim 13 wherein said parallel cuts are made at an angle of approximately 15° rotation from said longitudinal axis.

19. The apparatus of claim 13 further comprising a second jaw rotatable relative to said tip support structure in an opposite sense to said first jaw by said force, said second jaw disposed adjacent said first jaw on a pivot seat for closely seating and rotatably engaging said lug with a negative form of said solid of revolution with a gap provided slightly larger than the distance between said parallel cuts.

20. A miniature articulating tip assembly comprising:
(a) a tip support structure having a longitudinal axis and including a lug, said lug being of a solid of revolution with a portion cut away parallel to the lug axis, with the parallel cut being made at an angle of approximately 15° rotation from said longitudinal axis; and
(b) a jaw rotatable relative to said tip support structure by a force applied parallel to said longitudinal axis of said tip support structure, said jaw having a pivot seat adapted for closely seating and rotatably engaging said lug when said jaw is rotated through an operational range of closed and open positions and for disengaging said jaw relative to said lug when said jaw is rotated to a disengagement position beyond said operational range.

21. The apparatus of claim 20 wherein said solid of revolution is a cylinder.

22. The apparatus of claim 20 wherein said solid of revolution is of hourglass shape.

23. The apparatus of claim 20 wherein said lug is fabricated as a single piece with said tip support structure.

24. The apparatus of claim 20 wherein two parallel cuts are made on said solid of revolution.

25. The apparatus of claim 24 wherein said two parallel cuts are made on said solid of revolution defining between each other equal arcs on said solid of revolution of approximately 40°.

26. The apparatus of claim 24 wherein each said parallel cut is made at an angle of approximately 15° rotation from said longitudinal axis.

27. The apparatus of claim 20 wherein said disengagement position is 40° beyond the open end of said operational range.

28. A miniature articulating tip assembly comprising:
(a) a tip support structure having proximal and distal ends and providing a wall;
(b) a first pivot lug connected to a first side of said wall, said lug being of a solid of revolution with a portion cut away parallel to the lug axis;
(c) a second pivot lug connected to the second side of said wall, said second lug being of a solid of revolution with a portion cut away parallel to the lug axis;
(d) a first jaw rotatable relative to said tip support structure by a force applied proximally and distally, said jaw having a pivot seat adapted for closely seating and rotatably engaging said first lug when said jaw is rotated through an operational range of closed and open positions and for disengaging said jaw relative to said lug when said jaw is rotated to a disengagement position beyond said operational range; and
(e) a second jaw rotatable relative to said tip support structure in an opposite sense to said first jaw by said force, said second jaw having a pivot seat adapted for closely seating and rotatably engaging said first lug when said jaw is rotated through an operational range of closed and open positions and for disengaging said jaw relative to said lug when said jaw is rotated to a disengagement position beyond said operational range.

29. The apparatus of claim 28 wherein said solids of revolution are cylinders.

30. The apparatus of claim 28 wherein said solids of revolution are of hourglass shape.

31. The apparatus of claim 28 wherein said lugs are fabricated as a single piece with said wall.

32. The apparatus of claim 28 wherein two parallel cuts are made on each said solids of revolution.

33. The apparatus of claim 32 wherein each said pair of parallel cuts made on said solids of revolution define between each other equal arcs of approximately 40° on each said solid of revolution.

34. The apparatus of claim 32 wherein each said parallel cut is made at an angle of approximately 15° rotation from the direction of said force.

35. The apparatus of claim 32 wherein said disengagement positions are 40° beyond the open ends of said operational ranges.

36. A miniature articulating instrument comprising:
(a) a handle assembly;
(b) a drive shaft reciprocally movable proximally and distally from said handle assembly;
(c) a tip support structure connected to said handle assembly and including a lug, said lug being of a solid of revolution with a portion cut away parallel to the lug axis; and
(d) a jaw connected to said drive shaft and rotatable relative to said tip support structure by a force applied proximally and distally, said jaw having a pivot seat adapted for closely seating and rotatably engaging said lug when said jaw is rotated through an operational range of closed and open positions and for disengaging said jaw relative to said lug when said jaw is rotated to a disengagement position beyond said operational range.

37. The apparatus of claim 36 wherein said lug is fabricated as a single piece with said tip support structure.

38. The apparatus of claim 36 wherein said handle assembly comprises (i) a fixed portion connected to said tip support structure and (ii) a movable portion connected to said drive shaft.

39. The apparatus of claim 38 wherein said fixed and movable portions of said handle assembly each comprise a finger loop.

40. The apparatus of claim 36 wherein said jaw is connected to said drive shaft by a link to said drive shaft adapted to transmit force in the distal direction from said drive shaft to said jaw at a distal portion of said link.

41. A miniature articulating instrument comprising:
(a) a handle assembly;
(b) a drive shaft reciprocally movable proximally and distally from said handle assembly;
(c) a tip support structure connected to said handle assembly and providing a wall;
(d) a first pivot lug connected to a first side of said wall, said lug being of a solid of revolution with a portion cut away parallel to the lug axis;
(e) a second pivot lug connected to the second side of said wall, said second lug being of a solid of revolution with a portion cut away parallel to the lug axis;
(f) a first jaw connected to said drive shaft and rotatable relative to said tip support structure by a force applied proximally and distally, said jaw having a pivot seat adapted for closely seating and rotatably engaging said first lug when said jaw is rotated through an operational range of closed and open positions and for disengaging said jaw relative to said lug when said jaw is rotated to a disengagement position beyond said operational range; and (e) a second jaw connected to said drive shaft and rotatable relative to said tip support structure in an opposite sense to said first jaw by said force, said second jaw having a pivot seat adapted for closely seating and rotatably engaging said first lug when said jaw is rotated through an operational range of closed and open positions and for disengaging said jaw relative to said lug when said jaw is rotated to a disengagement position beyond said operational range.

42. The apparatus of claim 41 wherein said lugs are fabricated as a single piece with said wall.

43. The apparatus of claim 41 wherein said handle assembly comprises (i) a fixed portion connected to said tip support structure and (ii) a movable portion connected to said drive shaft.

44. The apparatus of claim 43 wherein said fixed and movable portions of said handle assembly each comprise a finger loop.

45. The apparatus of claim 41 wherein said jaws are connected to said drive shaft by links to said drive shaft adapted to transmit force in the distal direction from said drive shaft to said jaws at distal portions of said links.

46. A miniature articulating instrument comprising:

(a) a handle assembly;

(b) a drive shaft reciprocally movable proximally and distally from said handle assembly;

(c) a tip support structure connected to said handle assembly and defining parallel walls on either side of a longitudinal axis including a lug connecting said walls, said lug being of a solid of revolution with a portion cut away parallel to the lug axis; and (b) a jaw connected to said drive shaft and rotatable relative to said tip support structure by a force applied proximally and distally, said jaw having a pivot seat for closely seating and rotatably engaging said lug with a negative form of said solid of revolution with a gap provided slightly larger than the maximum thickness of said lug measured normal to said parallel cut.

47. The apparatus of claim 46 wherein said lug is fabricated as a single piece with said walls.

48. The apparatus of claim 46 wherein said handle assembly comprises (i) a fixed portion connected to said tip support structure and (ii) a movable portion connected to said drive shaft.

49. The apparatus of claim 48 wherein said fixed and movable portions of said handle assembly each comprise a finger loop.

50. The apparatus of claim 46 wherein said jaw is connected to said drive shaft by a link to said drive shaft adapted to transmit force in the distal direction from said drive shaft to said jaw at a distal portion of said link.

51. The apparatus of claim 46 further comprising a second jaw rotatable relative to said tip support structure in an opposite sense to said first jaw by said force, said second jaw disposed adjacent said first jaw on a pivot seat for closely seating and rotatably engaging said lug with a negative form of said solid of revolution with a gap provided slightly larger than the maximum thickness of said lug measured normal to said parallel cut.

52. The apparatus of claim 51 wherein said handle assembly comprises (i) a fixed portion connected to said tip support structure and (ii) a movable portion connected to said drive shaft.

53. The apparatus of claim 52 wherein said fixed and movable portions of said handle assembly each comprise a finger loop.

54. The apparatus of claim 51 wherein said jaws are connected to said drive shaft by links to said drive shaft adapted to transmit force in the distal direction from said drive shaft to said jaws at distal portions of said links.

\* \* \* \* \*